United States Patent
Lin et al.

(10) Patent No.: US 7,910,228 B2
(45) Date of Patent: Mar. 22, 2011

(54) MATERIALS FOR ORGANIC LIGHT-EMITTING DIODES

(75) Inventors: Jiann T'suen Lin, Taipei (TW); Mei-Yi Lai, Taoyuan (TW); Chih-Hsin Chen, Sanchang (TW)

(73) Assignee: Academia Sinica, Nankang Teipei (TW)

( * ) Notice: Subject to any disclaimer, the term of this patent is extended or adjusted under 35 U.S.C. 154(b) by 227 days.

(21) Appl. No.: 12/270,918

(22) Filed: Nov. 14, 2008

(65) Prior Publication Data

US 2009/0134783 A1    May 28, 2009

Related U.S. Application Data

(60) Provisional application No. 61/003,325, filed on Nov. 16, 2007.

(51) Int. Cl.
*H01J 1/63* (2006.01)
(52) U.S. Cl. .............. 428/690; 313/504; 548/309.7
(58) Field of Classification Search .......... None
See application file for complete search history.

(56) References Cited

U.S. PATENT DOCUMENTS

| 7,598,667 B2 * | 10/2009 | Kawamura et al. ........... 313/504 |
| 2003/0129448 A1 * | 7/2003 | Lin et al. ........................ 428/690 |

OTHER PUBLICATIONS

Zhang, et al., Efficient single-layer electroluminescent device based on a bipolar emitting boron-containing material, *Chem. Commun.*, 2006, 281-283.
Thomas et al., Cyanocarbazole Derivatives for High-Performance Electroluminescent Devices, *Adv. Funct. Mater.*, No. 4, Apr. (2004).
Huang et al., Dipolar dibenzothiophene S,S-Dioxide Derivatives Containing Diarylamine: Materials for Single-Layer Organic Light-Emitting Devices, *Adv. Mater.*, 2006, 18, 602-606.
Liao et al., A Novel Ambipolar Spirobifluorene Derivative that Behaves as an Efficient Blue-Light Emitter in Organic Light-Emitting Diodes, *Organic Letters*, vol. 9, No. 22, p. 4511-4514 (2007).

\* cited by examiner

*Primary Examiner* — D. Lawrence Tarazano
*Assistant Examiner* — Gregory Clark
(74) *Attorney, Agent, or Firm* — Cohen Pontani Lieberman & Pavane LLP

(57) ABSTRACT

The present invention provides for emissive materials comprising compounds of specific chemical structure, and electroluminescent devices comprising such emissive materials.

5 Claims, 11 Drawing Sheets

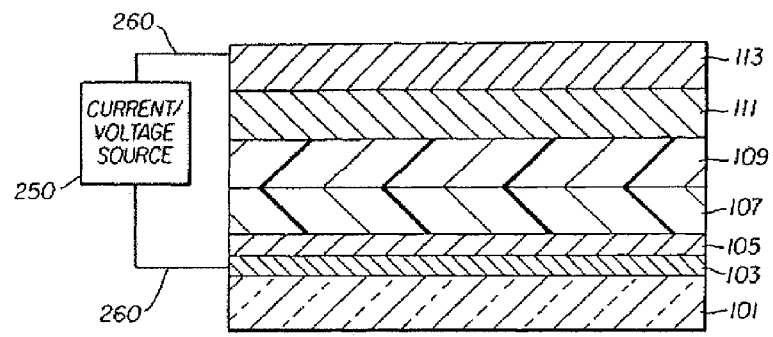
FIG. 1
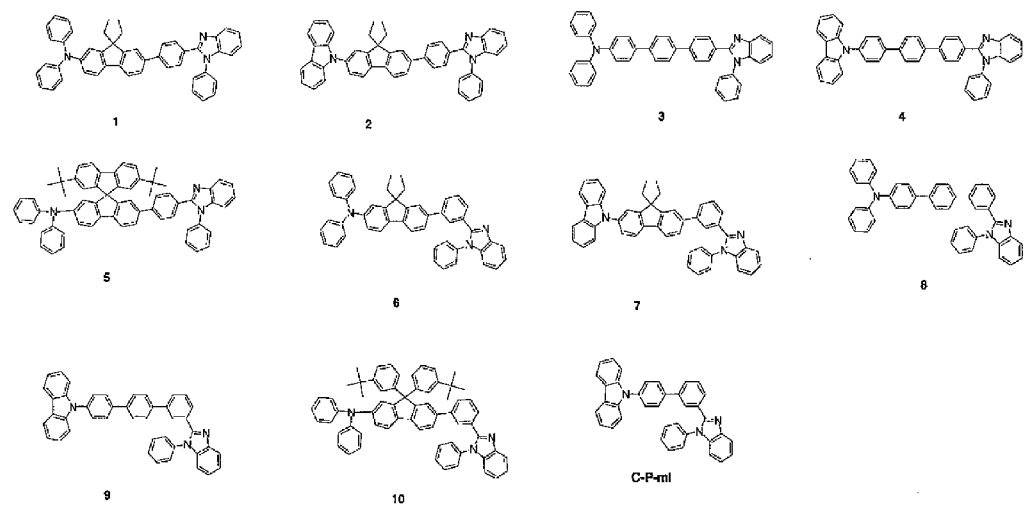
Figure 2. The structures of the ambipolar compounds.

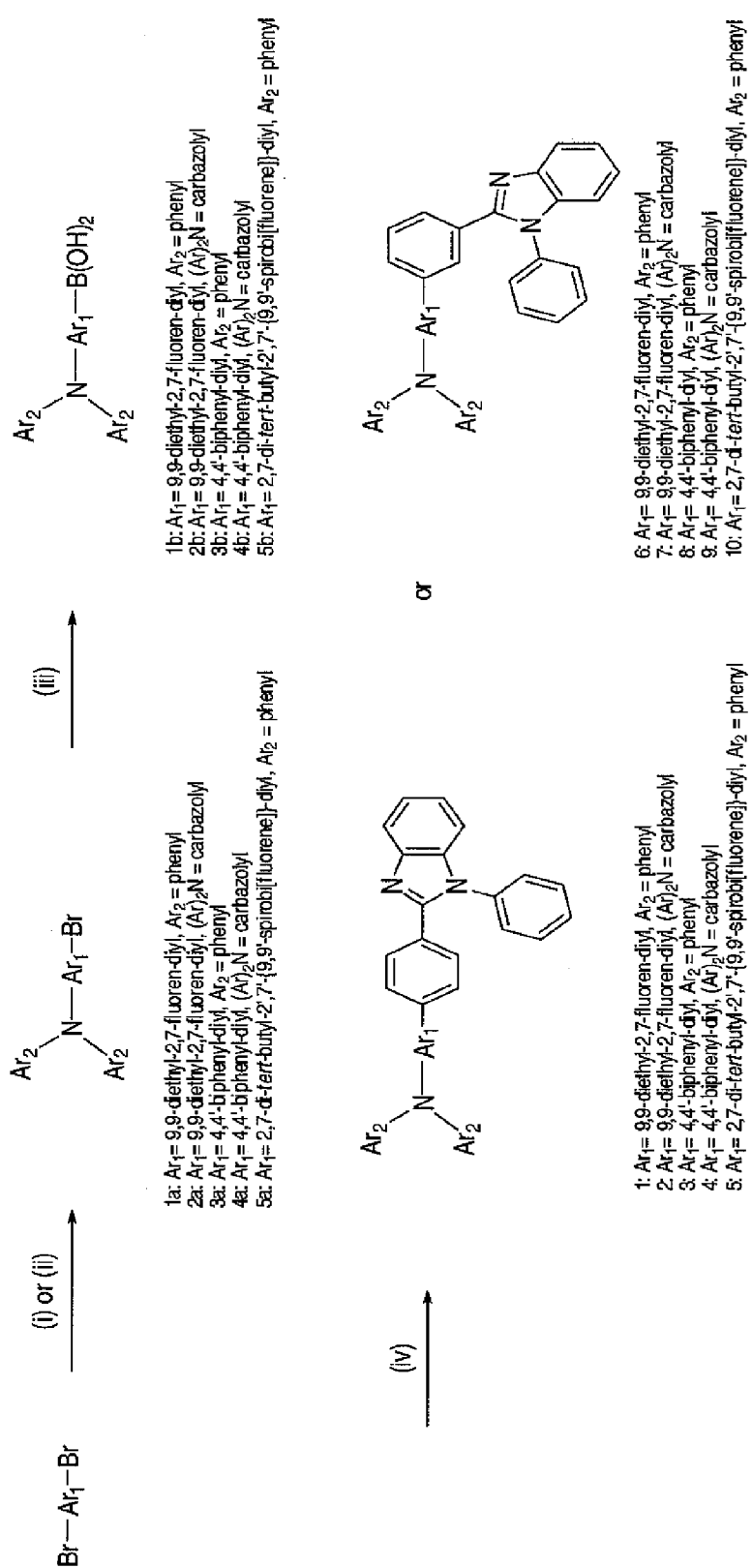
Figure 3 Reaction conditions: (i) diphenylamine, Pd(dba)₂, dppf, *t*-BuONa, toluene, 90 °C; (ii) carbazole, CuI, K₂CO₃, 18-crown-6, DMPU, 170 °C; (iii) *n*-BuLi, −78 °C, THF then B(OMe)₃; (iv) Pd(PPh₃)₄, 2M Na₂CO₃(aq), toluene, reflux

Synthesis
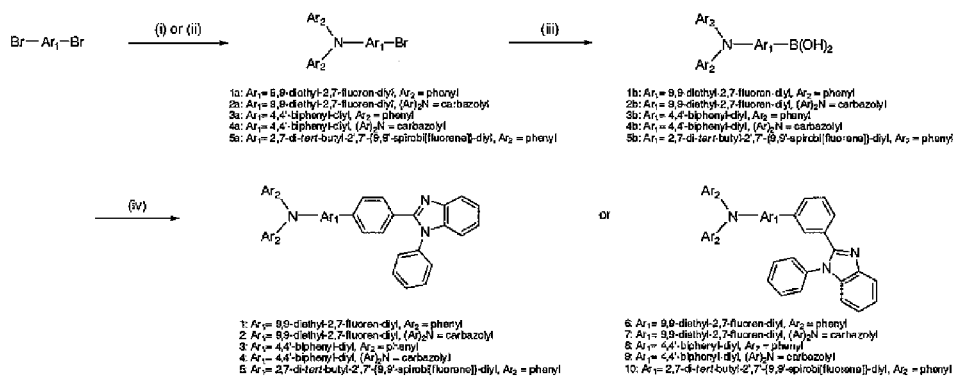
Figure 3 Reaction conditions: (i) diphenylamine, Pd(dba)$_2$, dppf, $t$-BuONa, toluene, 90 °C; (ii) carbazole, CuI, K$_2$CO$_3$, 18-crown-6, DMPU, 170 °C; (iii) $n$-BuLi, -78 °C, THF then B(OMe)$_3$; (iv) Pd(PPh$_3$)$_4$, 2M Na$_2$CO$_{3(aq)}$, toluene, reflux.
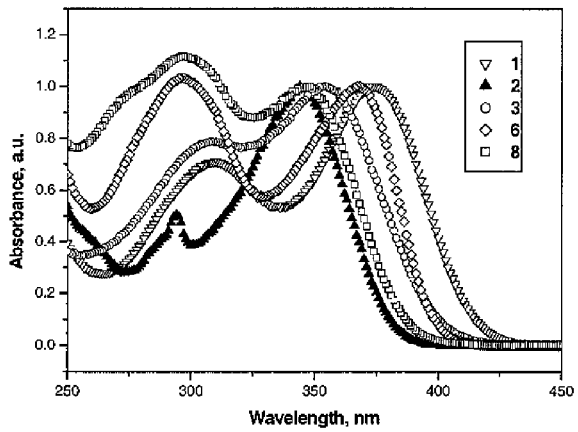
(a)

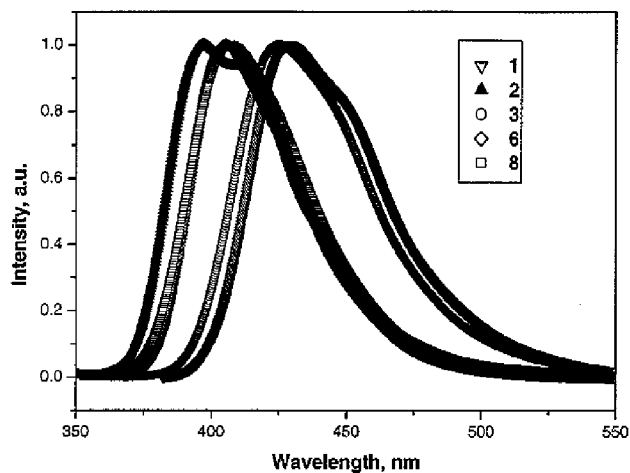
(b)
Figure 4. Absorption (a) and emission (b) spectra of 1, 2, 3, 6, and 8 recorded in $CH_2Cl_2$ solution.
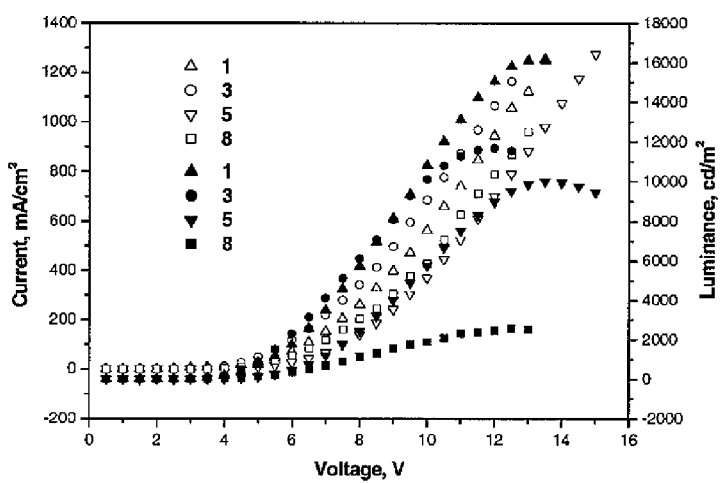

Figure 5. Current density and luminance verse applied electric field characteristic for devices I of 1, 3, 5, and 8. Device structure (I), ITO/compd (80 nm)/LiF 91 nm)/Al (150 nm)

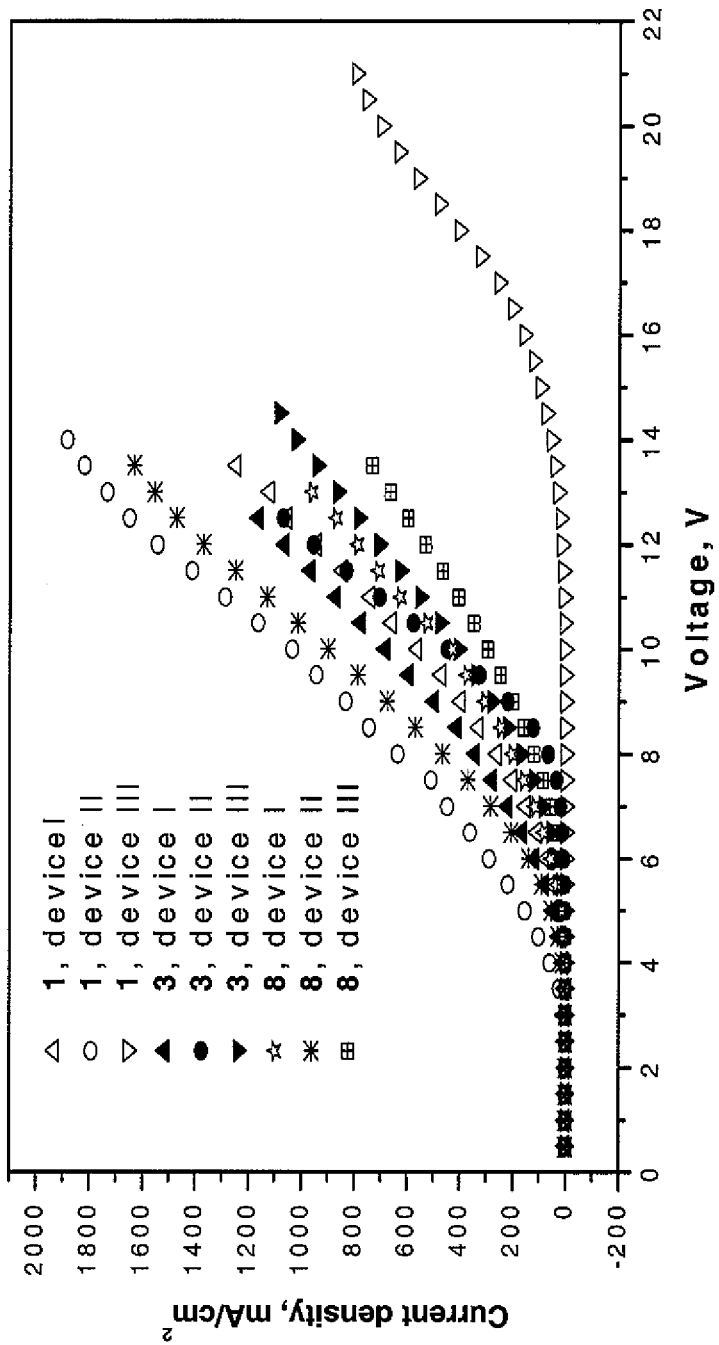
Figure 6 Current density and luminance verse applied electric field characteristic for devices I-III of 1, 3, and 8.
Device structure (I), ITO/compd (80 nm)/LiF 91 nm)/Al (150 nm); (II) ITO/NPB (40 nm)/compd (40 nm)/LiF (1 nm)/Al(150 nm); (III) ITO/compd (40 nm)/TPBI (40 nm)/LiF (1 nm)/Al(150 nm).

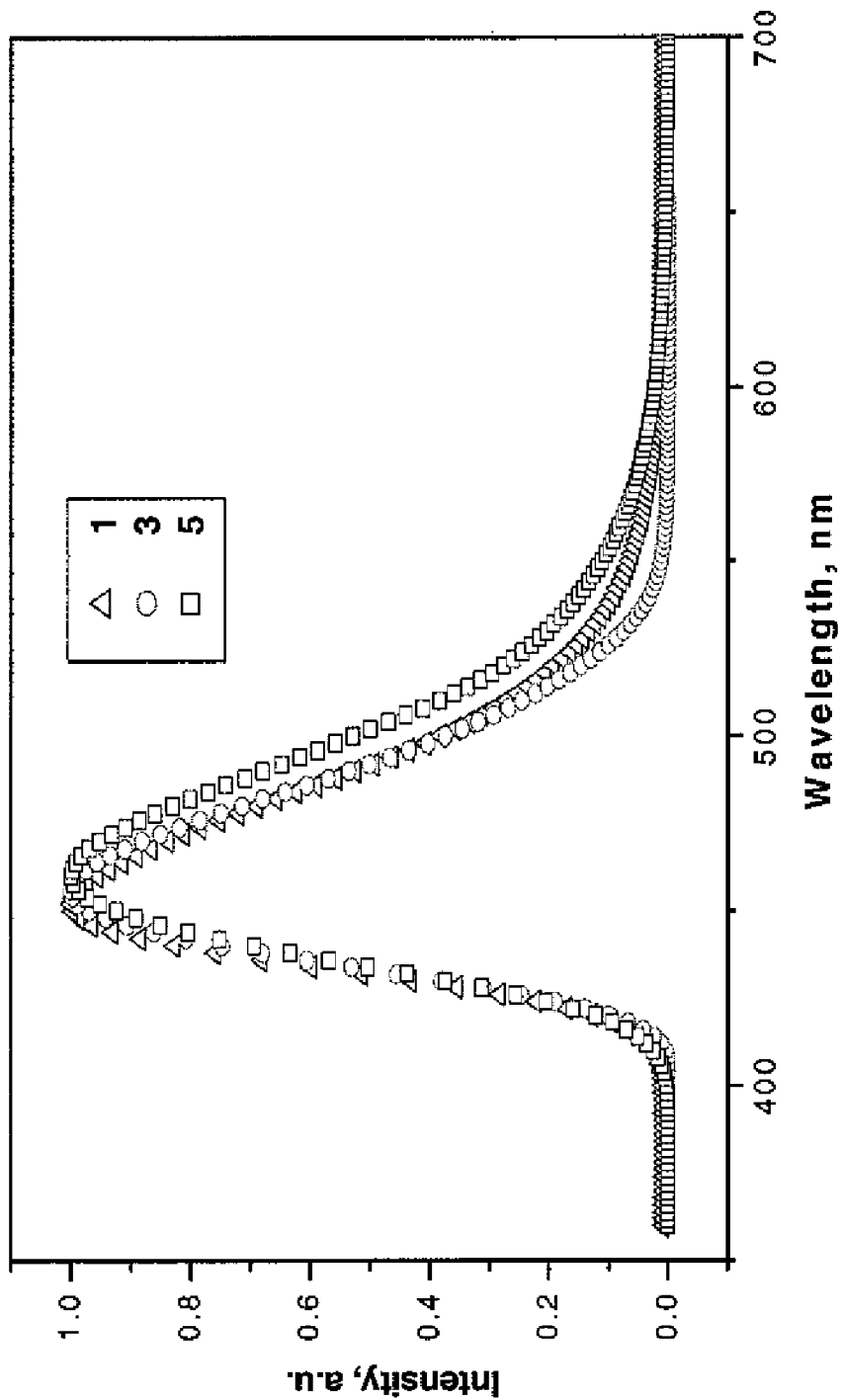
Figure 7. EL spectra for single-layer devices of 1, 3, and 5.

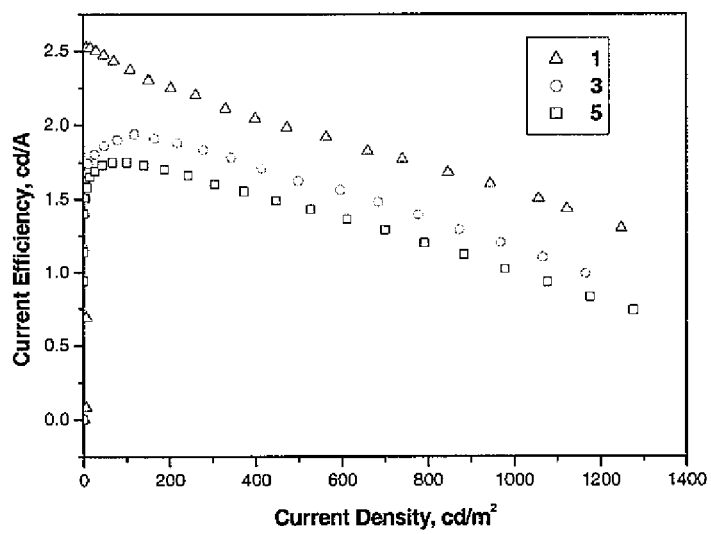
Figure 8. Current efficiency verse current density for single-layer devices of 1, 3, and 5.

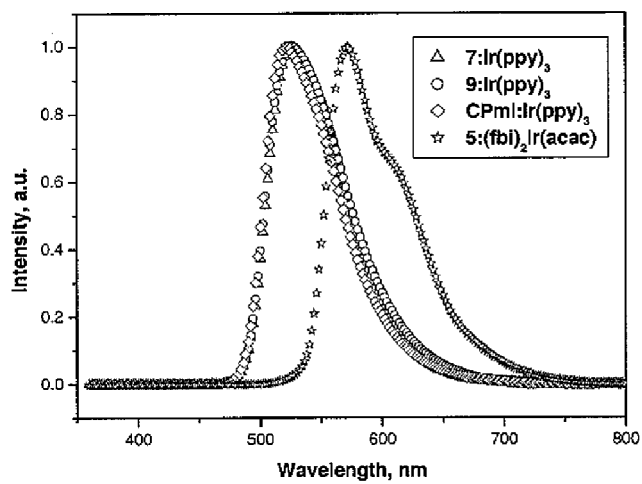
Figure 9. EL spectra for single-layer devices of 7, 9, and C-P-mI with 5% of Ir(ppy)$_3$ dopant, and 5 with 5% of (fbi)$_2$Ir(acac)$_3$ dopant.
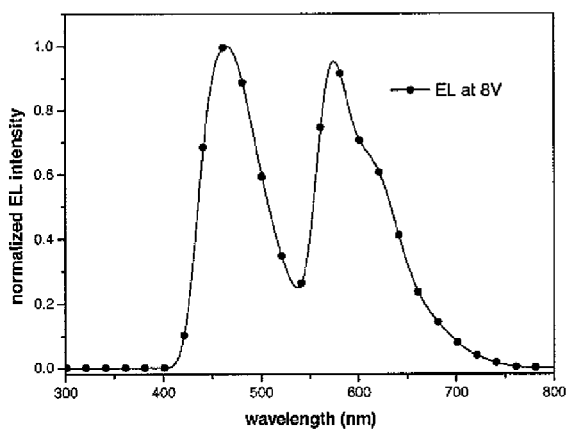
(a)

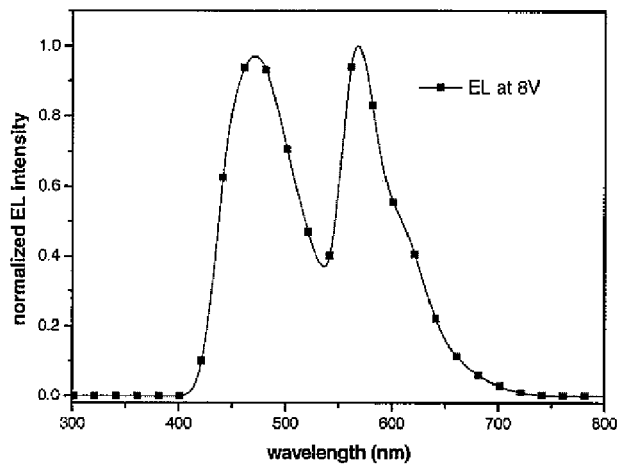
(b)
Figure 10. EL spectra for white light-emitting devices of 5: (a) device 1; (b) device 2.
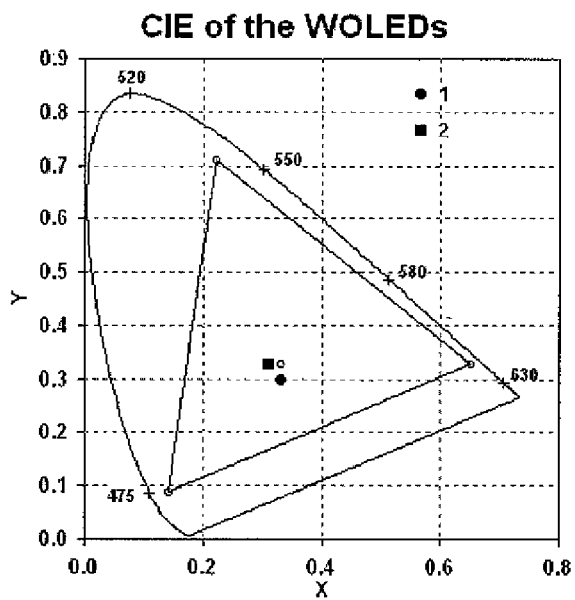
Figure 11 CIE coordinates of the three white light-emitting devices of 5.
1: ITO/N-SF-I doped Ir(fbi)2acac (8 nm)/N-SF-I (72 nm)/BCP (10 nm)/LiF/Al
Max Efficiency: 3.7 %, 7.6 cd/A, 4.5 lm/W , 22806 cd/m$^2$ 2. ITO/N-SF-I (72 nm)/N-SF-I doped Ir(fbi)2acac (8 nm)/BCP (10 nm)/LiF/Al Max Efficiency: 3.4 %, 8.0 cd/A, 5.4 lm/W , 36660 cd/m$^2$

MATERIALS FOR ORGANIC LIGHT-EMITTING DIODES

CROSS-REFERENCE TO RELATED APPLICATION

The present application claims priority to Provisional Patent Application 61/003,325, filed Nov. 16, 2007, the contents of which is incorporated by reference in its entirety,

BACKGROUND OF THE INVENTION

The organic light-emitting diodes OLED technology has stimulated intensive research activities across all disciplines. Currently, great efforts in materials research have been focused on novel materials for full-color flexible displays. Full-color displays require three basic colors, red, green and blue, and flexible substrates require low temperature and easy processing of the organic materials. OLED devices show great promise in meeting both requirements, since the emission color can be tailored by modulation of the chemical structures and the solution processing permits for micro-patterning of the fine multicolor pixels via inkjet printing technique (Yang, Y., et al., J. Mater. Sci.: Mater. Elecron., 2000, 11, 89). However, processable, stable, and efficient blue light-emitting organic materials are still highly desirable to meet the challenge. Blue light requires wide energy band. With blue light-emitting compounds as primary materials, it is possible to produce other colors by a downhill energy transfer process. For instance, a green or red electroluminescent EL emission can be obtained by doping a blue EL host material with a small amount of green or red luminescent material.

General EL Device Architecture

The present invention can be employed in most organic EL device configurations. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

The selection of benzimidazole/amine-based compounds of the present invention allows for a high-efficiency single-layer blue-emitting EL device. A Single-layer device is the preferred EL device structure of this invention, which is simpler and less costly to fabricate than multi-layer device structures. To our knowledge, no single-layer blue-emitting EL device has been previously reported that exhibit sufficient efficiency.

Outside of the single-layer device configuration, there are numerous configurations of the organic layers wherein the present invention can be successfully practiced. A typical structure is shown in FIG. 1 and includes a substrate 101, an anode 103, a hole-injecting layer 105, a hole-transporting layer 107, a light-emitting layer 109, an electron-transporting layer 111, and a cathode 113. These layers are described in detail below. FIG. 1 is for illustration only and the individual layer thickness is not scaled according to the actual thickness. Note that the substrate can alternatively be located adjacent to the cathode, or the substrate can actually constitute the anode or cathode. The organic layers between the anode and cathode are conveniently referred to as the organic EL element. Also, the total combined thickness of the organic layers is preferably less than 500 nm.

The anode and cathode of the OLED are connected to a voltage/current source 250 through electrical conductors 260. The OLED is operated by applying a potential between the anode and cathode such that the anode is at a more positive potential than the cathode. Holes are injected into the organic EL element from the anode and electrons are injected into the organic EL element at the anode. Enhanced device stability can sometimes be achieved when the OLED is operated in an AC mode where, for some time period in the cycle, the potential bias is reversed and no current flows. An example of an AC driven OLED is described in U.S. Pat. No. 5,552,678.

Substrate

The OLED device of this invention is typically provided over a supporting substrate 101 where either the cathode or anode can be in contact with the substrate. The electrode in contact with the substrate is conveniently referred to as the bottom electrode. Conventionally, the bottom electrode is the anode, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the EL layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. Of course it is necessary to provide in these device configurations a light-transparent top electrode.

Anode

When EL emission is viewed through anode 103, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode 103. The anode can be modified with plasma-deposited fluorocarbons. For applications where EL emission is viewed only through the cathode electrode, the transmissive characteristics of anode are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable way such as evaporation, sputtering, chemical vapor deposition, or electrochemical means. Anodes can be patterned using well-known photolithographic processes. Optionally, anodes can be polished prior to application of other layers to reduce surface roughness so as to reduce shorts or enhance reflectivity.

Hole-Injection Layer (HIL)

Although not always necessary, it is often useful that a hole-injecting layer 105 be provided between anode 103 and hole-transporting layer 107. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers, as described in U.S. Pat. No. 6,208,075, and some aromatic amines, for example, m-MTDATA (4,4',4"-tris[(3-methylphenyl)phenylamino] triphenylamine). Alternative hole-injecting materials reportedly useful in organic EL devices are described in EP 0 891 121 A1 and EP 1 029 909 A1.

Hole-Transporting Layer (HTL)

The hole-transporting layer 107 of the organic EL device in general contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel, et al., U.S. Pat. No. 3,180,730. Other suitable triarylamines substituted with one or more vinyl radicals or at least one active hydrogen-containing group are disclosed by Brantley, et al. in U.S. Pat. Nos. 3,567,450 and 3,658,520

Other Useful Organic Layers and Device Architecture

In some instances, the light-emitting layer 109 and the electron-transporting layer 111 can optionally be collapsed into a single layer that serves the function of supporting both light emission and electron transportation. Alternatively, the light-emitting layer 109 and the hole-transporting layer 107 can optionally be collapsed into a single layer that serves the function of supporting both light emission and hole transportation. Alternatively, layers 107, 109 and 111 can optionally be collapsed into a single layer that serves the function of supporting both light emission and hole and electron transportation. This is the preferred EL device structure of this invention and is referred to as "single-layer" device. In contrast to multi-layer device structures, fabrication of a single-layer device is simpler and less costly.

To our knowledge, no single-layer blue-emitting EL device has been previously reported that exhibit sufficient efficiency. The selection of benzimidazole/amine-based compounds of the present invention allows for a high-efficiency single-layer blue-emitting EL device.

It also known in the art that emitting dopants can be added to the hole-transporting layer, which can serve as a host. Multiple dopants can be added to one or more layers in order to produce a white-emitting EL device, for example, by combining blue- and yellow-emitting materials, cyan- and red-emitting materials, or red-, green-, and blue-emitting materials. White-emitting devices are described, for example, in EP 1 187 235, EP 1 182 244, U.S. patent application Publication 2002/0025419 A1, and U.S. Pat. Nos. 5,683,823, 5,503,910, 5,405,709, and 5,283,182.

Additional layers such as electron or hole-blocking layers as taught in the art can be employed in devices of this invention, Hole-blocking layers are commonly used to improve efficiency of phosphorescent emitter devices, for example, as in U.S. patent application Publication 2002/0015859 A1.

This invention can be used in so-called stacked device architecture, for example, as taught in U.S. Pat. Nos. 5,703,436 and 6,337,492.

BRIEF SUMMARY OF THE INVENTION

Benzimidazole/Amine-Based Compounds for use in OLED Devices Deposition of Organic Layers The organic materials of the present invention comprise a complex fluorene or spirofluorene structure and can be used as host, dopant, charge transporting material, charge blocking material, or combination thereof.

The organic materials mentioned above can be deposited as high quality transparent thin films by various methods such as a vapor deposition or sublimation method, an electron-beam method, a sputtering method, a thermal transferring method, a molecular lamination method and a coating method such as solution casting, spin-coating or inkjet printing, with an optional binder to improve film formation. If the material is a polymer, solvent deposition is typically preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can use separate sublimator boats or the materials can be premixed and coated from a single boat or donor sheet. Patterned deposition can be achieved using shadow masks, integral shadow masks (U.S. Pat. No. 5,294,870), spatially defined thermal dye transfer from a donor sheet (U.S. Pat. Nos. 5,688,551, 5,851,709, and 6,066,357), and inkjet method (U.S. Pat. No. 6,066,357).

Preferably, the spin-coating or inkjet printing technique is used to deposit the organic material of the invention, only one compound is deposited in a single layer device.

We have found that a number of benzimidazole/amine-based compounds can be used in highly efficient OLED devices. Compounds 1 to 10 of FIG. 2 are synthesized by processes discussed below and schematically described in FIG. 3. The physical properties of the compounds are described in Table 1. The NMR analysis of the compounds and LED fabrication using some of the compounds are also discussed below.

BRIEF DESCRIPTION OF THE DRAWINGS

In the drawings:

FIG. 1 schematically shows the configuration of a single-layer electroluminescent device.

FIG. 2 shows the chemical structures of each of the compounds of the present invention.

FIG. 3 shows the reaction steps for the synthesis of the compounds of the present invention.

FIG. 4 shows the Absorption (a) and emission (b) spectra of 1, 2, 3, 6, and 8 recorded in $CH_2Cl_2$ solution.

FIG. 5 shows the current density and luminance versus applied electric field characteristic for device of structure I using compounds 1, 3, 5, and 8. The Device of structure (I) comprises ITO/compd (80 nm)/LiF 91 nm)/Al (150 nm)

FIG. 6 shows the current density and luminance verse applied electric field characteristic for devices of structure I-III of 1, 3, and 8. The device structure (I) comprises ITO/compd (80 nm)/LiF 91 nm)/Al (150 nm); the device of structure (II) comprises ITO/NPB (40 nm)/compd (40 nm)/LiF (1 nm)/Al (150 nm); and the device of structure comprises (III) ITO/compd (40 nm)/TPBI (40 nm)/LiF (1 nm)/Al (150 nm).

FIG. 7 shows the EL spectra for single-layer devices of compounds 1, 3, and 5.

FIG. 8 shows the current efficiency verse current density for single-layer devices of compounds 1, 3, and 5.

FIG. 9 shows the EL spectra for single-layer devices of 7, 9, and C-P-ml with 5% of Ir(ppy)$_3$ dopant, and 5 with 5% of (fbi)$_2$Ir(acac)$_3$ dopant.

FIG. 10 shows the EL spectra for white light-emitting devices of 5: (a) device 1; (b) device 2.

FIG. 11 shows the CIE coordinates of the three white light-emitting devices of 5.

DETAILED DESCRIPTION OF THE INVENTION

The following describes specific processes for the making and the properties of the compounds of the present invention.

2-(4-Bromophenyl)-1-phenyl-1H-benzo[d]imidazole (p-BPBI). To a flask containing N-phenyl-o-phenylenediamine (9.21 g, 50 mmol) and 4-bromobenzaldehyde (9.25 g, 50 mmol) was added 50 mL of 20-methoxyethanol. After the mixture was refluxed for 48 h, the volatile was removed under vacuum and the residue was extracted with CH$_2$Cl$_2$. The organic extract was washed with brine, dried over anhydrous MgSO$_4$, filtered and pumped dry. The crude product was purified by column chromatography using a mixture of CH$_2$Cl$_2$ and n-hexane (1:1 by vol.) as the eluent. Analytically pure 2-(4-bromophenyl)-1-phenyl-1H-benzo[d]imidazole was isolated as a white solid in 72% (9.77 g) yield. $^1$H NMR (400 MHz, CDCl$_3$): δ 7.68 (d, 1 H, J=8.0 Hz), 7.35-7.29 (m, 4 H), 7.24-7.20 (m, 1 H), 7.15-7.02 (m, 7 H). MS (FAB): m/z 348.9 (M$^+$). Anal. calcd. for C$_{19}$H$_{13}$BrN$_2$: C, 65.35; H, 3.75; N, 8.02. Found: C, 65.22; H, 3.78; N, 8.01.

2-(3-Bromophenyl)-1-phenyl-1H-benzo[d]imidazole (m-BPBI) was prepared as the same procedure as 2-(4-bromophenyl)-1-phenyl-1H-benzo[d]imidazole from N-phenyl-o-phenylenediamine and 4-bromobenzaldehyde. The isolated yield of the compound was 85%. It has the same spectroscopic data as that as the bona fide compound.[11]

Syntheses of 1a-5a

Compounds 7-bromo-9,9-diethyl-N,N-diphenyl-9H-fluoren-2-amine (1a), 4'-bromo-N,N-diphenylbiphenyl-4-amine (3a), and 7-bromo-2',7'-di-tert-butyl-N,N-diphenyl-9,9'-spirobi[fluoren]-2-amine (5a) were synthesized by similar procedures. Compounds 9-(7-bromo-9,9-diethyl-9H-fluoren-2-yl)-9H-carbazole (2a) and 9-(4'-bromobiphenyl-4-yl)-9H-carbazole (4a) were synthesized by similar procedures. Only the preparation of 1a and 2a will be described in detail.

Compound 1a. To a flask containing a mixture of 2,7-dibromo-9,9-diethyl-9H-fluorene (4.18 g, 11.0 mmol), diphenylamine (0.85 g, 5.0 mmol), sodium tert-butoxide (0.72 g, 7.5 mmol), Pd(dba)$_2$ (0.032 g, 0.055 mmol) and 1,1'-Bis(diphenylphosphino)ferrocene (dppf) (0.033 g, 0.06 mmol) was added dry toluene (80 mL). The reaction mixture was heated to 80° C. and stirred for 16 h then 100° C. for 24 h. After cooling, the solution was removed under reduced pressure and the residue was extracted with CH$_2$Cl$_2$/brine. The organic layer was dried over magnesium sulfate, then filtered and dried. The crude product was further purified by column chromatography using CH$_2$Cl$_2$/hexane (1:10 by vol) as eluent to give the 1a as a white powder (2.11 g, 90%). $^1$H NMR (400 MHz, CDCl$_3$): δ 7.51 (d, 1 H, J=8.0 Hz), 7.38-7.47 (m, 3 H), 7.21-7.26 (m, 4 H), 7.09 (d, 4 H, J=8.0 Hz), 6.97-7.06 (m, 4 H), 1.84-2.02 (m, 4 H), 0.34 (t, 6 H, J=7.3 Hz); MS (FAB): m/z 468.1 [M$^+$+H].

Compound 2a. A mixture of 2,7-dibromo-9,9-diethyl-9H-fluorene (2.85 g, 7.5 mmol), carbazole (0.85 g, 7.5 mmol), CuI (0.14 g, 0.75 mmol), 18-Crown-6 (0.066 g, 0.25 mmol), K$_2$CO$_3$ (2.07 g, 15.0 mmol) and 1,3-dimethyl-3,4,5,6-tetrahydro-2(1H)-pyrimidinone (DMPU) (2 mL) was heated to 170° C. for 16 h under nitrogen. After cooling to room temperature, the mixture was quenched with 1 N HCl then extracted with CH$_2$Cl$_2$/brine. The organic layer was dried over magnesium sulfate, then filtered and dried. The crude product was further purified by column chromatography using CH$_2$Cl$_2$/hexane (1:10 by vol) as eluent to give the 2a as a white powder (2.10 g, 60%). $^1$H NMR (400 MHz, CDCl$_3$): δ 8.15 (d, 2 H, J=7.7 Hz), 7.86 (d, 1 H, J=8.0 Hz), 7.62 (d, 1 H, J=8.0 Hz), 7.47-7.54 (m, 4 H), 7.37-7.44 (m, 4 H), 7.26-7.31 (m, 2 H), 1.86-2.06 (m, 4 H), 0.43 (t, 6 H, J=7.3 Hz); MS (FAB): m/z 465.1 [M$^+$].

Compound 3a. White powder (yield: 81%). $^1$H NMR (400 MHz, CDCl$_3$): δ 7.52 (d, 2 H, J=8.0 Hz), 7.39-7.43 (m, 4 H), 7.26 (dd, 4 H, J=8.0, 8.0 Hz), 7.09-7.13 (m, 6 H), 7.03 (t, 2 H, J=8.0 Hz); MS (FAB): m/z 400.7 [M$^+$+H].

Compound 4a. White powder (yield: 65%). $^1$H NMR (400 MHz, CDCl$_3$): δ 8.14 (d, 2 H, J=7.7 Hz), 7.76 (d, 2 H, J=8.0 Hz), 7.62 (dd, 4 H, J=8.0, 8.0 Hz), 7.54 (d, 2 H, J=8.0 Hz), 7.39-7.47 (m, 4 H), 7.29 (t, 2 H, J=8.0 Hz); MS (FAB): m/z 397.1 [M$^+$].

Compound 5a. White powder (yield: 70%) $^1$H NMR (400 MHz, CDCl$_3$): δ 7.67 (d, 1 H, J=8.0 Hz), 7.62 (d, 2 H, J=8.0 Hz), 7.60 (d, 1 H, J=8.0 Hz), 7.43 (dd, 1 H, J=8.0, 1.7 Hz), 7.35 (dd, 2 H, J=8.0, 1.7 Hz), 7.07 (t, 4 H, J=8.0 Hz), 7.01 (dd, 1 H, J=8.0, 1.7 Hz), 6.90 (d, 4 H, J=8.0 Hz), 6.86 (t, 2 H, J=8.0 Hz), 6.80 (d, 1 H, J=1.7 Hz), 6.72 (d, 2 H, J=1.7 Hz), 6.55 (d, 1 H, J=1.7 Hz), 1.21 (s, 18 H); MS (FAB): m/z 673.2 [M$^+$].

Syntheses of 1b-5b

The boron reagents (1b-5b) of 1a-5a were synthesized by similar procedures. Only the preparation of 7-(diphenylamino)-9,9-diethyl-9H-fluoren-2-ylboronic acid (1b) will be described in detail.

Compound 1b. A solution of n-butyllithium (16.7 mL, 1.6 M in hexane) was added dropwise to a solution of 7-bromo-9,9-diethyl-N,N-diphenyl-9H-fluoren-2-amine (1a) (2.11 g, 4.5 mmol) in THF (40 mL) prechilled to −78° C. After the solution was stirred at −78° C. for 1 h, B(OMe)$_3$ (1.51 mL, 13.5 mmol) was added slowly. After addition, the solution was stirred at −78° C. for 30 minutes then back to room temperature overnight. The reaction was quenched by adding 50 mL of dilute HCl solution (10%), and the mixture was extracted with dichloromethane. The combined organic layer was washed with brine solution and dried over anhydrous MgSO$_4$. After filtration and removal of the solvent, the product 1b was yielded as a pale yellow solid (1.93 g, 99%) and used for next step without further purification.

Syntheses of 1-10

Compounds 9,9-diethyl-N,N-diphenyl-7-(4-(1-phenyl-1H-benzo[d]imidazol-2-yl)phenyl)-9H-fluoren-2-amine (1), 9-(9,9-diethyl-7-(4-(1-phenyl-1H-benzo[d]imidazol-2-yl)phenyl)-9H-fluoren-2-yl)-9H-carbazole (2), N,N-diphenyl-4'-(4-(1-phenyl-1H-benzo[d]imidazol-2-yl)phenyl)-biphenyl-4-amine (3), 9-(4'-(4-(1-phenyl-1H-benzo[d]imidazol-2-yl)phenyl)-biphen-4-yl)-9H-carbazole (4), 2',7'-di-tert-butyl-N,N-diphenyl-7-(4-(1-phenyl-1H-benzo[d]imidazol-2-yl)phenyl)-9,9'-spirobi[fluorene]-2-amine (5), 9,9-diethyl-N,N-diphenyl-7-(3-(1-phenyl-1H-benzo[d]imidazol-2-yl)phenyl)-9H-fluoren-2-amine (6), 9-(9,9-diethyl-7-(3-(1-phenyl-1H-benzo[d]imidazol-2-yl)phenyl)-9H-fluoren-2-yl)-9H-carbazole (7), N,N-diphenyl-4'-(3-(1-phenyl-1H-benzo[d]imidazol-2-yl)phenyl)-biphenyl-4-amine (8), 9-(4'-(3-(1-phenyl-1H-benzo[d]imidazol-2-yl)phenyl)-biphen-4-yl)-9H-carbazole (9), and 2',7'-di-tert-butyl-N,N-diphenyl-7-(3-(1-phenyl-1H-benzo[d]imidazol-2-yl)phenyl)-9,9'-spirobi[fluorene]-2-amine (10) were synthesized by similar procedures. Only the preparation of 1 will be described in detail.

Compound 1. To the flask containing a mixture of 7-(diphenylamino)-9,9-diethyl-9H-fluoren-2-ylboronic acid (1b)

(1.91 g, 4.0 mmol), 2-(4-bromophenyl)-1-phenyl-1H-benzo[d]imidazole (1.40 g, 4.4 mmol), Na$_2$CO$_3$ (2 M in H$_2$O, 8.0 mL, 16.0 mmol), and Pd(PPh$_3$)$_4$ (0.19 g, 0.16 mmol) was added 40 mL of dry toluene. After the reaction mixture was refluxed for 48 h, the solvent was removed and the residue was extracted with CH$_2$Cl$_2$/brine. The organic layer was dried over magnesium sulfate, then filtered and dried. The crude product was further purified by column chromatography using CH$_2$Cl$_2$/hexane (1:1 to 5:1 by vol) as eluent to give the 1 as a pale yellow solid (2.1 g, 71%) $^1$H NMR (400 MHz, CDCl$_3$): δ 7.91 (d, 1 H, J=8.0 Hz), 7.49-7.68 (m, 12 H), 7.35-7.38 (m, 3 H), 7.22-7.26 (m, 5 H), 7.13-7.09 (m, 5 H), 6.97-7.04 (m, 3 H), 1.85-2.02 (m, 4 H), 0.36 (t, 6 H, J=7.3 Hz). $^{13}$C NMR (125 MHz, CDCl$_3$): δ 152.3, 151.8, 150.8, 148.2, 147.6, 143.2, 142.7, 141.4, 138.3, 137.6, 137.4, 136.3, 130.1, 130.0, 129.4, 128.8, 128.5, 127.7, 127.0, 126.3, 124.1, 123.8, 123.6, 123.3, 122.7, 121.4, 120.7, 120.0, 119.6, 119.5, 100.6, 56.4, 32.9, 8.8. FAB MS (m/z): 658.3 [M$^+$+H]. HRMS (m/z): Calcd for C$_{48}$H$_{40}$N$_3$: 658.3222. Found: 658.3218 [M$^+$+H]. Anal. calcd. for C$_{48}$H$_{39}$N$_3$: C, 87.64; H, 5.98; N, 6.39. Found: C, 87.77; H, 5.88; N, 6.32.

Compound 2. Pale brown solid (yield: 60%). $^1$H NMR (400 MHz, CDCl$_3$): δ 8.16 (d, 2 H, J=7.7 Hz), 7.98 (d, 1 H, J=8.0 Hz), 7.91 (d, 1 H, J=8.0 Hz), 7.81 (d, 1 H, J=8.0 Hz), 7.73 (d, 2 H, J=8.0 Hz), 7.66 (d, 2 H, J=8.0 Hz), 7.62 (dd, 2 H, J=8.0, 1.4 Hz), 7.51-7.60 (m, 6 H), 7.38-7.43 (m, 7 H), 7.24-7.33 (m, 4 H), 1.98-2.15 (m, 4 H), 0.46 (t, 6 H, J=7.3 Hz). $^{13}$C NMR (125 MHz, CDCl$_3$): δ 152.1, 151.5, 151.0, 142.8, 141.0, 140.6, 140.3, 139.1, 136.9, 136.6, 130.1, 130.0, 129.0, 127.5, 127.1, 126.3, 126.0, 125.9, 123.9, 123.7, 123.3, 121.8, 121.5, 121.0, 120.3, 120.2, 119.9, 119.3, 110.6, 109.7, 56.0, 32.8, 8.7. FAB MS (m/z): 656.3 [M$^+$+H]. HRMS (m/z): Calcd for C$_{48}$H$_{38}$N$_3$: 656.3066. Found: 656.3060 [M$^+$+H]. Anal. calcd. for C$_{48}$H$_{37}$N$_3$: C, 87.91; H, 5.69; N, 6.41. Found: C, 87.82; H, 5.76; N, 6.34.

Compound 3. White solid (yield: 75%). $^1$H NMR (400 MHz, CDCl$_3$): δ 7.94 (d, 1 H, J=8.0 Hz), 7.67 (d, 2 H, J=8.0 Hz), 7.63 (d, 2 H, J=8.0 Hz), 7.61 (d, 2 H, J=8.0 Hz), 7.56 (d, 2 H, J=8.0 Hz), 7.48-7.54 (m, 5 H), 7.34-7.39 (m, 3 H), 7.23-7.30 (m, 6H), 7.13 (d, 6 H, J=8.0 Hz), 7.03 (t, 2 H, J=8.0 Hz). $^{13}$C NMR (125 MHz, CDCl$_3$): δ 151.8, 147.6, 147.4, 142.2, 141.7, 140.0, 138.2, 137.1, 136.8, 134.2, 130.0, 129.9, 129.3, 128.8, 128.1, 127.6, 127.4, 127.3, 126.9, 126.7, 124.5, 123.7, 123.6, 123.3, 123.0, 119.5, 110.5. FAB MS (m/z): 590.3 [M$^+$+H]; HRMS (m/z): Calcd for C$_{43}$H$_{32}$N$_3$: 590.2596. Found: 590.2601 [M$^+$+H]. Anal. calcd. for C$_{43}$H$_{31}$N$_3$: C, 87.58; H, 5.30; N, 7.13. Found: C, 87.49; H, 5.39; N, 7.03.

Compound 4. White solid (yield: 63%). $^1$H NMR (400 MHz, CDCl$_3$): δ 8.15 (d, 2 H, J=7.7 Hz), 7.99 (d, 1 H, J=8.0 Hz), 7.84 (d, 2 H, J=8.0 Hz), 7.70-7.77 (m, 6 H), 7.64 (d, 4 H, J=8.0 Hz), 7.52-7.60 (m, 3 H), 7.47 (d, 2 H, J=8.0 Hz), 7.38-7.44 (m, 5H), 7.25-7.34 (m, 4 H). $^{13}$C NMR (125 MHz, CDCl$_3$): δ 151.3, 142.1, 140.8, 139.8, 139.5, 139.1, 137.9, 136.7, 136.4, 130.2, 130.1, 129.2, 128.8, 128.4, 128.3, 127.6, 127.5, 127.4, 127.3, 127.0, 126.0, 124.1, 123.9, 123.4, 120.3, 120.0, 119.2, 110.7, 109.8. FAB MS (m/z): 588.2 [M$^+$+H]. HRMS (m/z): Calcd for C$_{43}$H$_{30}$N$_3$: 588.2440. Found: 588.2438 [M$^+$+H]. Anal. calcd. for C$_{43}$H$_{29}$N$_3$: C, 87.88; H, 4.97; N, 7.15. Found: C, 87.65; H, 4.70; N, 6.90.

Compound 5. Pale yellow solids (yield: 66%). $^1$H NMR (400 MHz, CDCl$_3$): δ 7.92 (d, 1 H, J=8.0 Hz), 7.79 (d, 1 H, J=8.0 Hz), 7.71 (d, 1 H, J=8.0 Hz), 7.47-7.62 (m, 8 H), 7.19 (d, 1 H, J=8.0 Hz), 7.06 (t, 4 H, J=8.0 Hz), 7.00 (dd, 1 H, J=8.0, 1.8 Hz), 6.84-6.90 (m, 7 H), 6.73 (d, 2 H, J=1.5 Hz), 6.53 (d, 1 H, J=1.5 Hz), 1.19 (s, 18H). $^{13}$C NMR (125 MHz, CDCl$_3$): δ 151.5, 150.7, 150.2, 148.6, 147.5, 141.4, 139.2, 138.4, 136.3, 130.2, 129.8, 129.0, 127.4, 126.9, 126.7, 124.7, 124.4, 124.0, 123.5, 122.4, 120.8, 120.6, 120.4, 119.7, 119.2, 110.7, 66.1, 34.8, 31.5. FAB MS (m/z): 864.4 for [M$^+$+H]. HRMS (m/z): Calcd for C$_{64}$H$_{54}$N$_3$: 864.4318. Found: 864.4322 [M$^+$+H]. Anal. Calcd for C$_{64}$H$_{53}$N$_3$: C, 88.96; H, 6.18; N, 4.86. Found: C, 89.34; H, 6.19; N, 4.84.

Compound 6. White solid (yield: 68%). $^1$H NMR (400 MHz, CDCl$_3$): δ 7.96 (d, 1 H, J=8.0 Hz), 7.80 (s, 1 H), 7.68 (t, 2 H, J=8.0 Hz), 7.54-7.61 (m, 4 H), 7.33-7.44 (m, 5 H), 7.20-7.30 (m, 8 H), 7.09-7.13 (m, 5 H), 6.98-7.04 (m, 3 H), 1.89-2.03 (m, 4 H), 0.34 (t, 6 H, J=7.3 Hz). $^{13}$C NMR (125 MHz, CDCl$_3$): δ 151.6, 150.7, 148.0, 147.4, 142.3, 141.3, 137.4, 136.0, 135.1, 130.6, 130.2, 129.6, 129.2, 128.6, 128.5, 127.5, 126.0, 125.7, 123.9, 123.9, 123.8, 123.6, 122.5, 121.3, 120.5, 119.4, 119.3, 117.8, 111.3, 56.3, 32.7, 8.6. FAB MS (m/z): 658.3 [M$^+$+H]. HRMS (m/z): Calcd for C$_{48}$H$_{40}$N$_3$: 658.3222. Found: 658.3214 [M$^+$+H]. Anal. calcd. for C$_{48}$H$_{39}$N$_3$: C, 87.64; H, 5.98; N, 6.39. Found: C, 87.28; H, 6.04; N, 6.42.

Compound 7. Pale brown solid (yield: 58%). $^1$H NMR (400 MHz, CDCl$_3$): δ 8.16 (d, 2 H, J=7.7 Hz), 8.03 (d, 1 H, J=8.0 Hz), 7.88-7.92 (m, 2 H), 7.78 (d, 1 H, J=8.0 Hz), 7.69-7.73 (m, 2 H), 7.59-7.63 (m, 3 H), 7.51-7.55 (m, 2 H), 7.40-7.47 (m, 9 H), 7.27-7.36 (m, 5 H), 2.03-2.15 (m, 4 H), 0.43 (t, 6 H, J=7.3 Hz). $^{13}$C NMR (125 MHz, CDCl$_3$): δ 152.1, 151.4, 151.0, 141.7, 141.1, 140.4, 139.3, 136.5, 130.2, 129.2, 129.1, 129.0, 128.4, 127.6, 126.3, 126.0, 125.9, 124.3, 124.1, 123.4, 121.8, 121.6, 120.9, 120.4, 120.1, 119.9, 119.2, 110.8, 109.7, 56.6, 32.8, 8.7. FAB MS (m/z): 656.3 [M$^+$+H]. HRMS (m/z): Calcd for C$_{48}$H$_{35}$N$_3$: 656.3066. Found: 656.3064 [M$^+$+H]. Anal. calcd. for C$_{48}$H$_{37}$N$_3$: C, 87.91; H, 5.69; N, 6.41. Found: C, 88.10; H, 5.88; N, 6.39.

Compound 8. White solid (yield: 70%). $^1$H NMR (400 MHz, CDCl$_3$): δ 7.97 (d, 1 H, J=8.0 Hz), 7.84 (s, 1 H), 7.58-7.64 (m, 2 H), 7.53-7.57 (m, 5 H), 7.48 (d, 2 H, J=8.0 Hz), 7.42 (d, 2 H, J=8.0 Hz), 7.35-7.40 (m, 4 H), 7.23-7.33 (m, 6 H), 7.11-7.14 (m, 6 H), 7.03 (t, 2 H, J=8.0 Hz). $^{13}$C NMR (125 MHz, CDCl$_3$): δ 151.6, 147.6, 147.3, 140.8, 139.9, 138.3, 136.6, 136.5, 134.2, 130.1, 129.3, 129.0, 128.5, 128.3, 128.2, 127.6, 127.5, 127.3, 126.9, 124.4, 124.0, 123.8, 123.0, 119.3, 110.7. FAB MS (m/z): 590.2 [M$^+$+H]; HRMS (m/z): Calcd for C$_{43}$H$_{32}$N$_3$: 590.2596. Found: 590.2603 [M$^+$+H]. Anal. calcd. for C$_{43}$H$_{31}$N$_3$: C, 87±58; H, 5.30; N, 7.13. Found: C, 87.49; H, 5.21; N, 7.03.

Compound 9. White solid (yield: 61%). $^1$H NMR (400 MHz, CDCl$_3$): δ 8.15 (d, 2 H, J=7.7 Hz), 8.06 (d, 1 H, J=8.0 Hz), 7.96 (s, 1 H), 7.84 (d, 2 H, J=8.0 Hz), 7.69-7.74 (m, 3 H), 7.59-7.66 (m, 6 H), 7.56 (d, 2 H, J=8.0 Hz), 7.34-7.50 (m, 9 H), 7.27-7.31 (m, 3 H). $^{13}$C NMR (125 MHz, CDCl$_3$): δ 150.5, 141.2, 140.8, 139.7, 139.5, 138.9, 137.1, 135.4, 130.5, 129.8, 129.4, 128.7, 128.6, 128.5, 128.4, 127.7, 127.6, 127.5, 127.4, 126.0, 125.2, 123.4, 120.3, 120.0, 118.3, 111.2, 109.8. FAB MS (m/z): 588.2 [M$^+$+H]. HRMS (m/z): Calcd for C$_{43}$H$_{30}$N$_3$: 588.2440. Found: 588.2438 [M$^+$+H]. Anal. calcd. for C$_{43}$H$_{29}$N$_3$: C, 87.88; H, 4.97; N, 7.15. Found: C, 87.67; H, 4.83; N, 7.05.

Compound 10. Pale yellow solids (yield: 62%). $^1$H NMR (500 MHz, CDCl$_3$): δ 7.94 (d, 1 H, J=8.0 Hz), 7.77 (d, 1 H, J=8.0 Hz), 7.68-7.71 (m, 3 H), 7.65 (d, 1 H, J=8.0 Hz), 7.46 (d, 1 H, J=8.0 Hz), 7.43 (d, 1 H, J=8.0 Hz), 7.38 (dd, 2 H, J=8.0, 1.8 Hz), 7.18-7.36 (m, 10 H), 7.07 (t, 4 H, J=8.0 Hz), 6.99 (dd, 1 H, J=8.0, 1.8 Hz), 6.84-6.90 (m, 6 H), 6.73 (d, 2 H, J=1.5 Hz), 6.50 (d, 1 H, J=1.5 Hz), 1.20 (s, 18H). $^{13}$C NMR (125 MHz, CDCl$_3$): δ 151.6, 151.5, 150.8, 149.8, 148.7, 147.6, 147.5, 141.4, 141.2, 139.2, 138.7, 136.4, 136.1, 129.9, 129.1, 128.9, 128.8, 128.3, 128.2, 126.9, 124.8, 124.3, 124.1, 123.9, 123.5, 122.4, 120.7, 120.6, 120.2, 119.6, 119.1, 110.7, 66.2, 34.9, 31.5. FAB MS (m/z): 864.4 for [M$^+$+H]. HRMS (m/z): Calcd for $C_{64}H_{54}N_3$: 864.4318. Found: 864.4320 [M$^+$+H]. Anal. Calcd for $C_{64}H_{53}N_3$: C, 88.96; H, 6.18; N, 4.86. Found: C, 89.21; H, 6.22; N, 4.95.

C-P-ml: Yield: 54%, $^1$H NMR (400 MHz, CDCl$_3$): δ 8.15 (d, 2 H, J=7.7 Hz), 8.06 (d, 1 H, J=8.0 Hz), 7.96 (s, 1 H), 7.84 (d, 2 H, J=8.0 Hz), 7.69-7.74 (m, 3 H), 7.59-7.66 (m, 6 H), 7.56 (d, 2 H, J=8.0 Hz), 7.34-7.50 (m, 9 H), 7.27-7.31 (m, 3 H). $^{13}$C NMR (125 MHz, CDCl$_3$): δ 150.5, 141.2, 140.8, 139.7, 139.5, 138.9, 137.1, 135.4, 130.5, 129.8, 129.4, 128.7, 128.6, 128.5, 128.4, 127.7, 127.6, 127.5, 127.4, 126.0, 125.2, 123.4, 120.3, 120.0, 118.3, 111.2, 109.8. FAB MS (m/z): 511.55 [M$^+$+H]. Anal. calcd. for $C_{37}H_{25}N_3$: C, 86.86; H, 4.93; N, 8.21. Found: C, 86.65; H, 4.81; N, 8.31

The absorption and emission spectra of compounds 1, 2, 3, 6 and 8 in CH$_2$Cl$_2$ solution is shown in FIG. 4. The electron and hole mobilities of compounds 1 to 8, CPMI and DCPMI are shown in Table 2.

LED Fabrication and Measurement

Devices of different structures were fabricated for EL studies: (1) ITO/1-2 (80 nm)/LiF (1 nm)/Al (150 nm); (II) ITO/NPB (40 nm)/1-2 (40 nm)/LiF (1 nm)/Al (150 nm); (III) ITO/1 (40 nm)/TPBI (40 nm)/LiF (1 nm)/Al (150 nm). Compounds NPB (1,4-bis[(1-naphthylphenyl)amino]biphenyl) and TPBI (1,3,5-tris(N-phenylbenzimidazol-2-yl)benzene) were used as the hole- and the electron-transporting materials, respectively, while LiF and Al were used as the electron-injection layer and the cathode. All devices are blue-emitting and representative EL spectra are shown in FIG. 7. The device performances are summarized in Table 3. Current-luminance (I-L) characteristics for representative devices of structure I are shown in FIG. 5. It is worth noting that the un-optimized single-layered devices I show very promising performances, for example: 2.4%; 1.2 lm/W; 2.4 cd/A; 2378 cd/m$^2$; (0.15, 0.12) at 100 mA/cm$^2$ for compound 1, and 1.4%; 0.9 lm/W; 1.8 cd/A; 1750 cd/m$^2$; (0.15, 0.15) at 100 mA/cm$^2$ for compound 5. Current-luminance (I-L) characteristics for representative devices of structures I to III are shown in FIG. 6. The performance of the single-layer devices of compounds 1, 3 and 5 compare favorably with those of non-doped blue-emitting devices reported in literature. See FIGS. 7 and 8. Among the devices I-III for the same compound, II has the best performance, but I gives performances similar to those of II. No discernible light emission was detected for the device III of 2. The device II of 1 appears to have the best performance among all blue-emitting devices reported here: 2.8%; 1.9 lm/A; 2.6 cd/A; 2626 cd/m$^2$ at 100 mA/cm$^2$.

When compound of the present invention are doped with Ir(ppy)$_3$ or Ir(acac), and used in a single layer device, the EL spectra is shown in FIG. 9. When the devices are structured as follows:

1: ITO/N-SF-I doped Ir(fbi)2acac (8 nm)/N-SF-I (72 nm)/BCP (10 nm)/LiF/Al Max Efficiency: 3.7%, 7.6 cd/A, 4.5 lm/W, 22806 cd/m$^2$
2: ITO/N-SF-I (72 nm)/N-SF-I doped Ir(fbi)2acac (8 nm)/BCP (10 nm)/LiF/Al Max Efficiency: 3.4%, 8.0 cd/A, 5.4 lm/W, 36660 cd/m$^2$

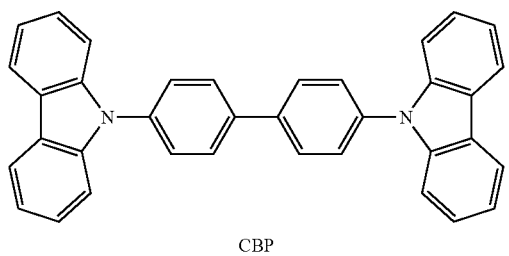

CBP

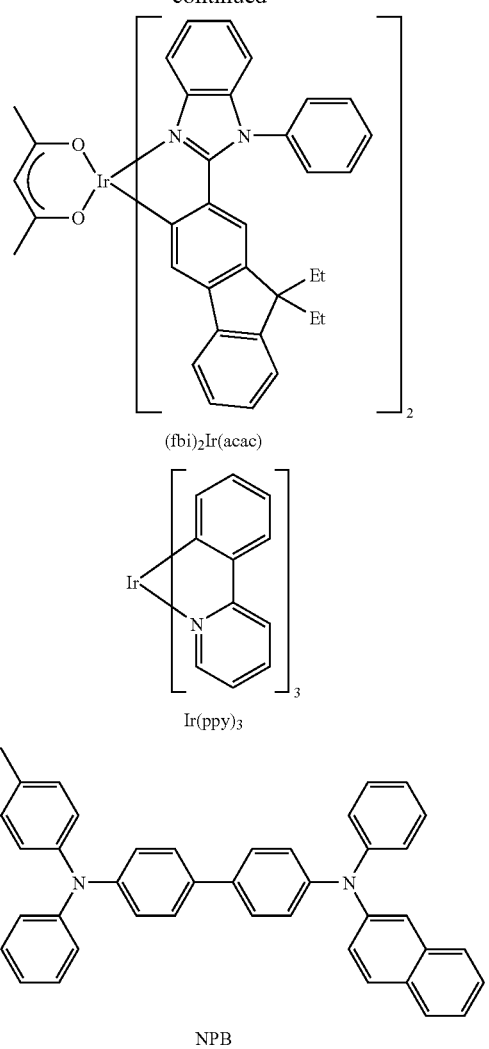

(fbi)$_2$Ir(acac)

Ir(ppy)$_3$

NPB

The EL spectra of the devices 1 and 2 of compound 5 is shown in FIG. 10. The Commission Internationale de l'Eclairage chromaticity coordinates of the same devices are shown in FIG. 11.

Construction of Device of Structure I

The hole-transporting material NPB (1,4-bis(1-naphthylphenylamino)-biphenyl) and electron-transporting materials TPBI (1,3,5-tris(N-phenylbezimidazol-2-yl)-benzene) were prepared by literature procedures, and was sublimed once prior to use. Pre-patterned ITO substrates with an effective individual device area of 3.14 mm$^2$ were cleaned by standard procedure before use. Double-layer EL devices were fabricated using compounds 1 or 2 as the electron-transporting and emitting layer or hole-transporting and emitting layer. The devices were prepared by vacuum deposition of 40 nm of NPB, followed by 40 nm of 1 or 2, or vacuum deposition of 40 nm of 1 or 2 followed by 40 nm of TPBI. Single-layer EL devices were prepared by vacuum deposition of 80 nm of 1 or 2. Inorganic LiF (1 nm thick) was then deposited as the buffer layer. Aluminum was finally deposited as the cathode (150 nm). I-V curves were measured in a Keithley 2400 Source Meter under the ambient environment. Light intensity was measured with a Newport 1835 Optical Meter.

In summary, we have developed a convenient synthesis of highly emissive compounds containing benzimidazole and arylamines. These blue-emitting compounds exhibit ambipolar carrier transport properties and are successfully used to fabricate single-layer blue-emitting EL devices with very promising performances compared to multi-layered blue-emitting devices. High-performance single-layer device with phosphorescent dopant using these compounds as the host is also demonstrated. The present invention teaches a new class of advanced materials for full-color OLED displays or white-emitting OLEDs.

TABLE 1

Physical properties of the compounds.

| compd | $T_m/T_g/T_d$,[a] °C. | $\lambda_{abs}$,[b] nm toluene | $\lambda_{abs}$,[b] nm $CH_2Cl_2$ | $\lambda_{em}(\Phi_f)$,[c] nm (%) toluene | $\lambda_{em}(\Phi_f)$,[c] nm (%) $CH_2Cl_2$ | $\lambda_{em}(\Phi_f)$,[c] nm (%) film | $E_T$,[d] eV | $E_{ox}(\Delta E_p)$,[e] mV | HOMO/LUMO,[f] eV |
|---|---|---|---|---|---|---|---|---|---|
| 1 | 284/104/373 | 310, 376 | 309, 372 | 428 (89) | 478 (65) | 466 (80) | 2.3 (2.2) | 386 (91) | 5.19/2.20 |
| 2 | na/135/439 | 294, 346 | 294, 344 | 397 (98) | 422 (92) | 433 | | 825 (120) | 5.63/2.38 |
| 3 | 212/106/430 | 355 | 354 | 425 (86) | 472 (64) | 457 | (2.2) | 484 (92) | 5.28/2.18 |
| 4 | 288/127/431 | 293, 329 | 294, 328 | 393 (76) | 415 (80) | 437 | | 855 (70) | 5.66/2.28 |
| 5 | 396/170/467 | 309, 376 | 315, 376 | 428 (76) | 475 (88) | 457 (72) | 2.3 (2.2) | 413 (70) | 5.21/2.21 |
| 6 | 226/100/392 | 296, 370 | 297, 367 | 405 (87) | 435 (95) | 430 | (2.3) | 385 (90) | 5.19/2.08 |
| 7 | 241/124/430 | 294, 328 | 294, 328 | 375 (83) | 393 (90) | 399 | | 818 (120) | 5.62/2.20 |
| 8 | na/99/398 | 346 | 296, 348 | 407 (77) | 439 (82) | 433 | (2.3) | 484 (92) | 5.28/2.08 |
| 9 | na/114/445 | 294, 310 | 293, 310 | 377 (97) | 400 (91) | | | 852 (114) | 5.65/2.16 |
| 10 | 280/152/441 | 314, 373 | 283, 369 | 407 (92) | 425 (89) | 426, 520 | | 412 (92) | 5.21/2.11 |

[a]The heating rate and cooling rate were 10° C./min and 30° C./min, respectively. $T_m$: melting point; $T_g$: glass transition temperature; $T_d$: decomposition temperature.
[b]$\lambda_{abs}$: absorption maximum.
[c]$\lambda_{em}$: emission maximum. Quantum yields ($\Phi_f$) were measured in solutions and in thin films, see ref. 14.
[d]$E_T$: triplet energy measured in toluene at 77 K (and in film).
[e]$E_{ox}$= 1/2($E_{pa}$ + $E_{pc}$), $\Delta E_p$ = $E_{pa}$ − $E_{pc}$ where $E_{pa}$ and $E_{pc}$ are anodic and cathodic potentials, respectively. Measured in $CH_2Cl_2$. All the potentials are reported relative to ferrocene, which was used as the internal standard in each experiment. Ferrocene oxidation potential was located at +272 mV relative to the Ag/AgNO$_3$ non-aqueous reference electrode.
[f]The HOMO and LUMO energies were determined from cyclic voltammetry and absorption onset.

TABLE 2

Electron and hole mobilities of compounds measured from the time-of-flight method.

| | $\mu_e \times 10^{-6}$ cm$^2$/(V·s) | $\mu_h \times 10^{-6}$ cm$^2$/(V·s) |
|---|---|---|
| 1 | 20-70 (nd) | 7-11 (nd) |
| 2 | | |
| 3 | 8-11 (nd) | 2-6 (nd) |
| 4 | | |
| 5 | 5-11 (nd) | 7-11 (nd) |
| 6 | 40-80 (nd) | 5-9 (nd) |
| 7 | | |
| 8 | 90-110 (d) | 9-11 (nd) |
| 9 | | |
| 10 | | |
| CPMI | 5-11 (d) | 0.1-0.6 (d) |
| DCPMI | 20-50 (d) | 10-30 (d) |

$\mu_e$: electron mobility; $\mu_e$: hole mobility; d: dispersive; nd: non-dispersive.

TABLE 3

Electroluminescent data of the devices.[a]

| | 1 | 3 | 5 | 6 | 8 | 10 |
|---|---|---|---|---|---|---|
| Von, V | 2.9; 2.7; 5.0 | 3.0; 3.5; 3.5 | 2.9; 2.7; | 3.5; 3.5; 4.5 | 3.5; 3.0; 3.5 | 5.0; 3.5; 4.0 |
| $L_{max}$, cd/m$^2$ (voltage, V) | 16178 (13.5) 21663 (14.0) 5713 (20.5) | 11669 (12.0) 25046 (12.5) 7351 (14.0) | 10011 (13.5); 10418 (14.0) | 2212 (12.0) 3553 (14.0) 1928 (15.0) | 2576 (12.5) 7988 (13.5) 2556 (13.0) | 1408 (15.5); 1333 (11.5) 3897 (13.5) |
| $\lambda_{em}$, nm | 452, 456, 446 | 456, 460, 454 | 458; 454 | 436, 440, 432 | 434, 440, 438 | 450, 450, 448 |
| CIE (x, y) | 0.15, 0.12; 0.14, 0.11; 0.15, 0.12 | 0.14, 0.09; 0.14, 0.12; 0.14, 0.07 | 0.15; 0.15 0.15, 0.12 | 0.15, 0.07; 0.15, 0.08; 0.15, 0.06 | 0.16, 0.07; 0.15, 0.06; 0.15, 0.05 | 0.22, 0.28; 0.19, 0.19; 0.17, 0.10 |
| fwhm, nm | 60; 62; 64 | 58; 62; 60 | 68; 62 | 62; 68; 56 | 56; 56; 56 | 142; 76; 64 |
| $\eta_{ext, max}$, % | 2.5; 3.0; 2.0 | 2.4; 4.7; 2.3 | 1.4; 1.6 | 0.85; 0.87; 2.3 | 1.0; 2.1; 3.5 | 0.28; 0.22; 1.5 |
| $\eta_{p, max}$, lm/W | 2.0; 2.3; 0.7 | 1.5; 3.0; 1.0 | 1.1; 1.6 | 0.43; 0.38; 0.54 | 0.46; 1.0; 1.2 | 0.29; 0.23; 0.85 |
| $\eta_{c, max}$, cd/A | 2.5; 2.8; 2.2 | 1.9; 4.6; 1.4 | 1.8; 1.7 | 0.56; 0.63; 1.1 | 0.62; 1.1; 1.7 | 0.60; 0.32; 1.3 |
| L,[b] cd/m$^2$ | 2378; 2626; 1125 | 1925; 3920; 1355 | 1750; 1432 | 513; 584; 548 | 589; 1052; 971 | 486; 302; 983 |

TABLE 3-continued

Electroluminescent data of the devices.[a]

| | 1 | 3 | 5 | 6 | 8 | 10 |
|---|---|---|---|---|---|---|
| $\eta_{ext}$[b] % | 2.4; 2.8; 1.2 | 2.4; 4.0; 2.2 | 1.4; 1.4 | 0.78; 0.82; 1.1 | 0.97; 1.9; 2.0 | 0.23; 0.20; 1.1 |
| $\eta_p$[b] lm/w | 1.2; 1.9; 0.24 | 1.1; 1.5; 0.59 | 0.9; 0.9 | 0.24; 0.26; 0.17 | 0.28; 0.59; 0.40 | 0.14; 0.14; 0.42 |
| $\eta_c$[b] cd/A | 2.4; 2.6; 1.2 | 1.9; 4.0; 1.4 | 1.8; 1.4 | 0.51; 0.59; 0.55 | 0.59; 1.1; 1.0 | 0.49; 0.30; 1.0 |

[a]The measured values are given in order of the devices I, II, and III. $L_{max}$, maximum luminance; $V_{on}$, turn-on voltage; V, voltage; $\lambda_{em}$, emission wavelength; CIE (x, y), Commission Internationale de l'Eclairage coordinates; fwhm, full width at half maximum; $\eta_{ext,\,max}$, maximum external quantum efficiency; $\eta_{p,\,max}$, maximum power efficiency; $\eta_{c,\,max}$, maximum current efficiency; L, luminance; $\eta_{ext}$, external quantum efficiency; $\eta_p$, power efficiency; $\eta_c$, current efficiency.
[b]at a current density of 100 mA/cm$^2$. $V_{on}$ was obtained from the x-intercept of log(luminance) vs applied voltage plot.
Device structure (I), ITO/compd (80 nm)/LiF 91 nm)/Al (150 nm); (II) ITO/NPB (40 nm)/compd (40 nm)/LiF (1 nm)/Al (150 nm); (III) ITO/compd (40 nm)/TPBI (40 nm)/LiF (1 nm)/Al(150 nm).

We claim:

1. An emissive material comprising a compound selected from the group having the formula:

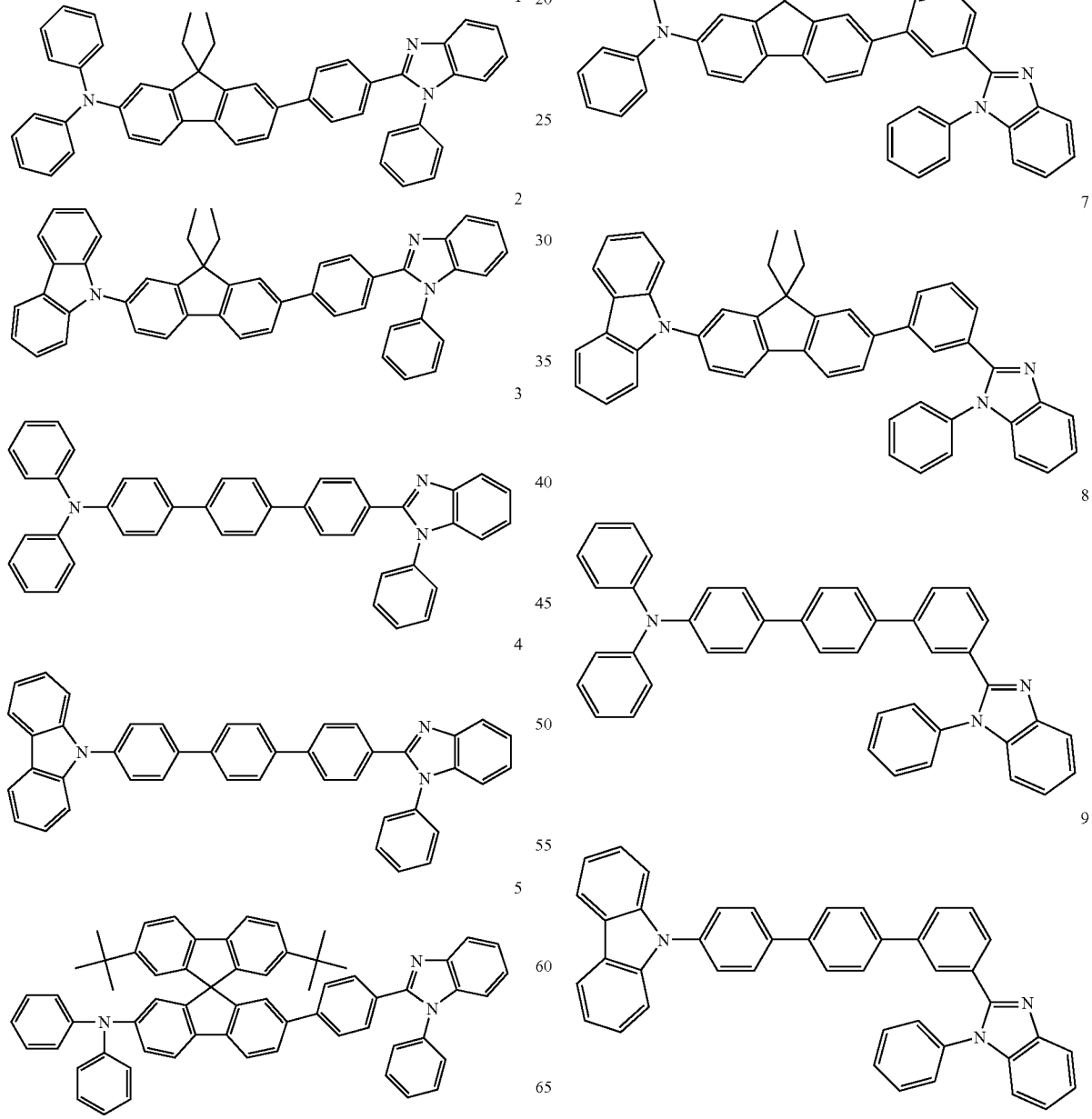

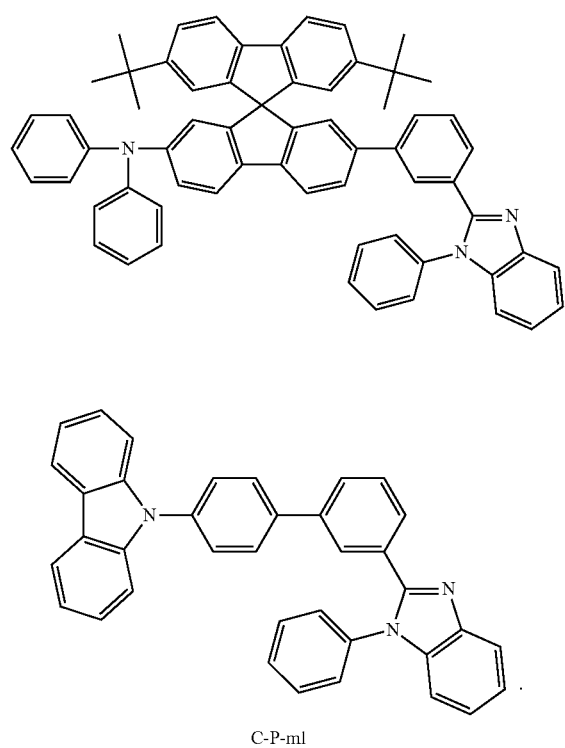

C-P-ml

2. An electroluminescent device, comprising: a) a spaced-apart anode and cathode; and b) an emissive layer of claim 1 disposed between the spaced-apart anode and cathode.

3. An electroluminescent device comprising: a hole transport layer; and an electron transport layer; wherein at least one of said hole transport layer and said electron transport layer comprises either alone or in combination a compound of the formula:

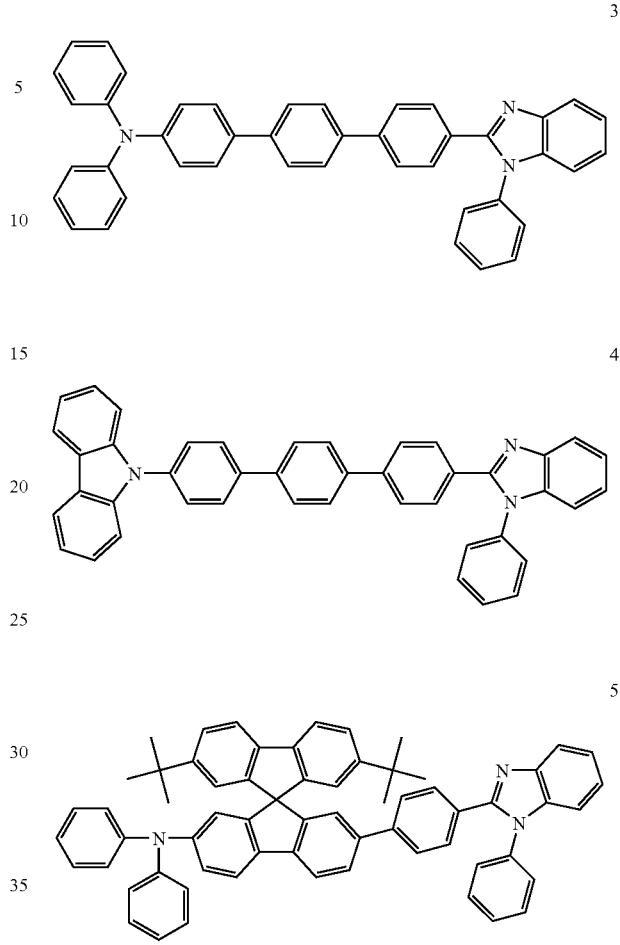

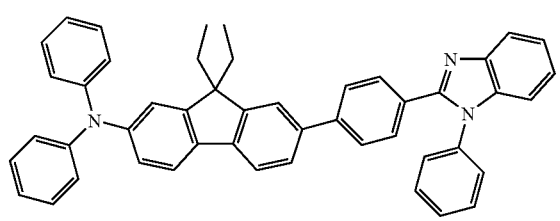

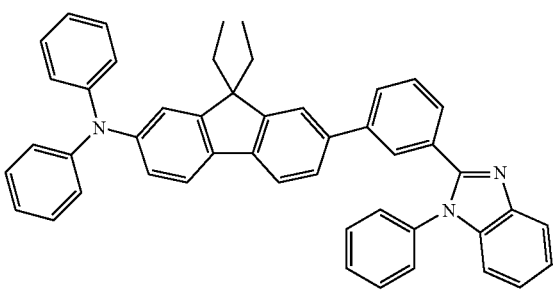

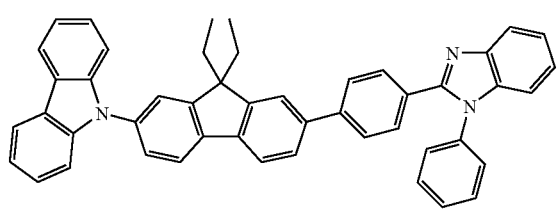

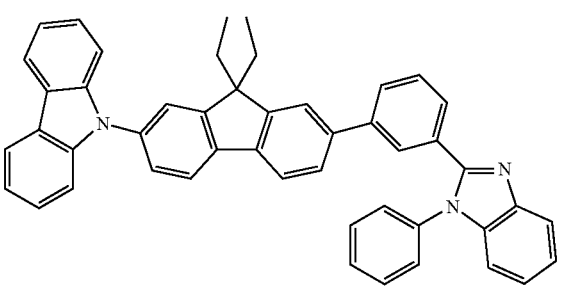

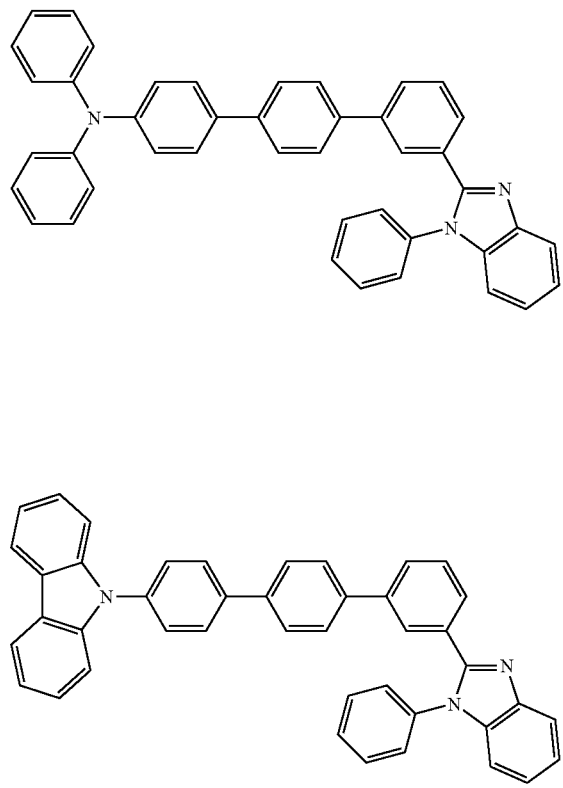
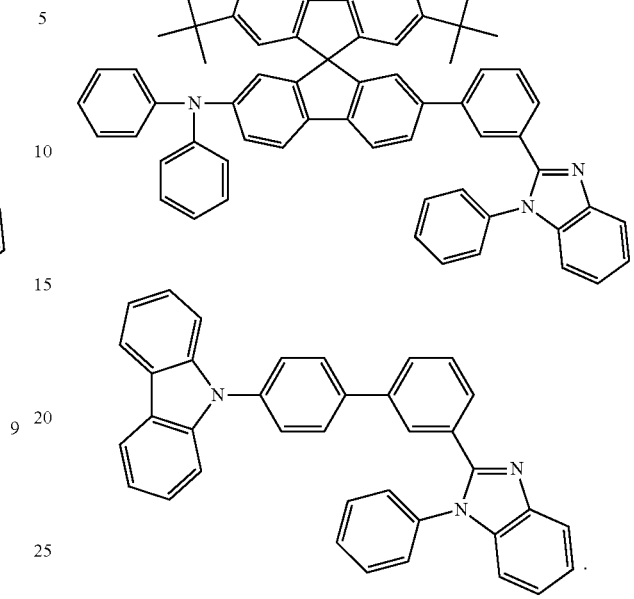
C-P-ml
4. The electroluminescent device of claim 3 wherein the hole transport layer further comprises an emitting dopant.
5. The electroluminescent device of claim 3 wherein the electron transport further comprises an emitting dopant.
* * * * *